United States Patent
Kim et al.

(10) Patent No.: US 11,291,726 B2
(45) Date of Patent: Apr. 5, 2022

(54) NEAR INFRARED ABSORBING DYE-BASED COMPOSITE PARTICLES EXHIBITING PHOTOTHERMAL EFFECT, METHOD FOR MANUFACTURING THE SAME, AND USE THEREOF

(71) Applicant: KOREA INSTITUTE OF SCIENCE AND TECHNOLOGY, Seoul (KR)

(72) Inventors: Sehoon Kim, Seoul (KR); Youngsun Kim, Seoul (KR); Keunsoo Jeong, Seoul (KR); Gayoung Kim, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 126 days.

(21) Appl. No.: 16/395,236

(22) Filed: Apr. 26, 2019

(65) Prior Publication Data

US 2020/0016269 A1 Jan. 16, 2020

(30) Foreign Application Priority Data

Jul. 11, 2018 (KR) .................. 10-2018-0080494

(51) Int. Cl.
*A61K 41/00* (2020.01)
*A61N 5/06* (2006.01)
*C09B 23/08* (2006.01)
*C09B 67/46* (2006.01)
(Continued)

(52) U.S. Cl.
CPC ...... *A61K 41/0057* (2013.01); *A61K 41/0028* (2013.01); *A61N 5/062* (2013.01); *C09B 23/086* (2013.01); *C09B 67/009* (2013.01); *C09B 67/0096* (2013.01); *C09B 67/0097* (2013.01); *A61N 2005/0659* (2013.01)

(58) Field of Classification Search
CPC ............ A61K 41/0057; A61K 41/0028; A61N 5/062; C09B 23/086
See application file for complete search history.

(56) References Cited

U.S. PATENT DOCUMENTS 6,344,272 B1 * 2/2002 Oldenburg ......... A61K 41/0042
  252/587
7,604,523 B1 * 10/2009 Wedding .................. H01J 11/18
  313/582

(Continued)

FOREIGN PATENT DOCUMENTS

KR 1020150035430 A 4/2015
KR 101630397 B1 6/2016

*Primary Examiner* — David P Porta
*Assistant Examiner* — Djura Malevic
(74) *Attorney, Agent, or Firm* — Cantor Colburn LLP

(57) ABSTRACT

The present invention relates to near-infrared-absorbing dye-based composite particles which exhibit a photothermal effect and/or photoacoustic signal upon photoirradiation, a preparation method thereof, and a use thereof. The near-infrared-absorbing composite particles comprise: a water-insoluble salt of a near-infrared-absorbing dye, which comprises anions of the near-infrared-absorbing dye and metal cations capable of forming a precipitation product with the anions of the near-infrared-absorbing dye; and particles of a polymeric surfactant, in which a water-insoluble salt of the near-infrared-absorbing dye is supported in the hydrophobic part of the polymeric surfactant.

19 Claims, 10 Drawing Sheets

(51) Int. Cl.
*C09B 67/54* (2006.01)
*C09B 67/02* (2006.01)

(56) References Cited

U.S. PATENT DOCUMENTS

| | | | | |
|---|---|---|---|---|
| 8,045,152 B2 * | 10/2011 | Halas | | G01N 21/80 |
| | | | | 356/301 |
| 8,067,737 B1 * | 11/2011 | Sayyah | | B82Y 30/00 |
| | | | | 250/336.1 |
| 8,350,223 B2 * | 1/2013 | Mintz | | G01J 1/58 |
| | | | | 250/365 |
| 8,376,013 B2 * | 2/2013 | Bourke, Jr. | | A61L 2/088 |
| | | | | 156/379.6 |
| 8,409,863 B2 * | 4/2013 | Natan | | G01N 21/658 |
| | | | | 436/79 |
| 8,941,062 B2 * | 1/2015 | Wagner | | G01N 21/1702 |
| | | | | 250/338.1 |
| 9,232,618 B2 * | 1/2016 | Bourke, Jr. | | H01J 65/042 |
| 9,267,889 B1 * | 2/2016 | Klopfer | | G01N 21/6428 |
| 9,368,740 B2 * | 6/2016 | Tang | | C09K 11/883 |
| 9,567,514 B2 * | 2/2017 | Zhao | | C09K 11/883 |
| 10,080,275 B2 * | 9/2018 | Bourke, Jr. | | H01J 65/042 |
| 10,266,760 B2 * | 4/2019 | Zhao | | H01L 33/502 |
| 10,427,008 B2 * | 10/2019 | Sullivan | | A63B 37/0031 |
| 2010/0224821 A1 * | 9/2010 | Mandelbaum | | B22F 1/0096 |
| | | | | 252/62.53 |
| 2010/0261263 A1 * | 10/2010 | Vo-Dinh | | B82Y 30/00 |
| | | | | 435/287.1 |
| 2010/0330147 A1 * | 12/2010 | Hossainy | | A61L 29/16 |
| | | | | 424/426 |
| 2011/0021970 A1 * | 1/2011 | Vo-Dinh | | A61K 41/0042 |
| | | | | 604/20 |
| 2011/0022148 A1 * | 1/2011 | Ruane | | A61K 41/0028 |
| | | | | 623/1.1 |
| 2011/0117202 A1 * | 5/2011 | Bourke, Jr. | | A61N 1/44 |
| | | | | 424/490 |
| 2011/0126889 A1 * | 6/2011 | Bourke, Jr. | | H01L 31/055 |
| | | | | 136/253 |
| 2011/0129537 A1 * | 6/2011 | Vo-Dinh | | A61K 47/6923 |
| | | | | 424/490 |
| 2011/0275061 A1 * | 11/2011 | Weidemaier | | G01N 33/54333 |
| | | | | 435/6.1 |
| 2012/0057165 A1 * | 3/2012 | Natan | | G01N 33/532 |
| | | | | 356/445 |
| 2012/0064134 A1 * | 3/2012 | Bourke, Jr. | | A61K 8/23 |
| | | | | 424/401 |
| 2012/0212733 A1 * | 8/2012 | Kodali | | C09B 67/0097 |
| | | | | 356/301 |
| 2012/0237447 A1 * | 9/2012 | Lee | | A61K 49/1818 |
| | | | | 424/9.1 |
| 2013/0108552 A1 * | 5/2013 | Sharma | | C09K 11/02 |
| | | | | 424/9.32 |
| 2015/0283392 A1 * | 10/2015 | Bourke, Jr. | | C02F 1/32 |
| | | | | 604/20 |
| 2018/0311355 A1 * | 11/2018 | Oldham | | A61K 33/242 |
| 2020/0267313 A1 * | 8/2020 | Youn | | H04N 5/23287 |

* cited by examiner (a)

(b)

(a)

(b)

(a)

(b)

(a)

(b)

(a)

| Sample | AST level (U/L) | ALT level (U/L) |
|---|---|---|
| PBS | 114.9 ± 0.9 | 54.8 ± 1.4 |
| Free ICG | 143.4 ± 2.0 | 56.5 ± 1.2 |
| ICG-Fe NPs | 87.3 ± 1.1 | 48.4 ± 1.5 |

※ Normal range: AST level (54-298 U/L), ALT level (17-77 U/L)

(b)

bar = 100 μm
CV: Central vein

ICG Fluorescence

Cy5.5 Fluorescence

NEAR INFRARED ABSORBING DYE-BASED COMPOSITE PARTICLES EXHIBITING PHOTOTHERMAL EFFECT, METHOD FOR MANUFACTURING THE SAME, AND USE THEREOF

TECHNICAL FIELD

The present invention relates to near-infrared-absorbing dye-based composite particles which exhibit a photothermal effect and/or photoacoustic signal upon photoirradiation, a preparation method thereof, and a use thereof.

BACKGROUND ART

Photothermal therapy is a method for treatment in which heat-generating materials capable of absorbing light in the near-infrared region are accumulated in a position that requires high-heat therapy and irradiated with light (infrared rays, etc.). Since body tissues have a very low absorption rate of the light in the near-infrared region, the depth at which local treatment in vivo is possible is increased, and damage to tissues other than where the materials are accumulated is minimized.

The growth of tumors requires angiogenesis, and the thus-formed blood vessels have several characteristics which distinguish them from normal blood vessels in that their lymphatic drainage is sluggish and loose, thus causing leakage, etc. Due to these characteristics, therapeutic particles can actually be accumulated in cancer cells more than in other sites (Korean Patent Application Publication No. 10-2015-0035430).

An example of near-infrared photothermal therapy of cancer in vivo using a photothermal material is a hydrophilic cyanine dye containing a sulfonate group. Among the hydrophilic cyanine dyes containing a sulfonate group, indocyanine green is a near-infrared fluorescent dye whose use is approved by the US Food and Drug Administration (FDA) for the diagnosis of the systems of the heart, liver, and blood vessels as well as the lymphatic system. In particular, indocyanine green is known as an excellent probe for the imaging of metastatic lymph nodes and mapping of sentinel lymph nodes for early diagnosis of breast cancer.

However, hydrophilic cyanine dyes containing a sulfonate group have disadvantages in that they have low photostability, low photon yield, and low sensitivity. In particular, indocyanine green has disadvantages in that it is vulnerable to nonspecific aggregation and is chemically decomposed by external light, solvents, and changes in temperature, and in addition, indocyanine green has a problem in that it is well absorbed into serum proteins and removed through the kidneys (Korean Patent No. 10-1630397).

DETAILS OF THE INVENTION

Summary

An object of the present invention is to provide near-infrared-absorbing composite particles which can be dispersed into colloidal nanoparticles by maintaining a structural form in body fluids and exhibit a photothermal effect and/or photoacoustic signal.

A first aspect of the present invention provides a method for preparing a near-infrared-absorbing dye-based composite particle, comprising:

a first step, in which an ionizable near-infrared-absorbing dye, that is in a state dissolved in an aqueous medium, undergoes a precipitation reaction with an ionic compound capable of providing a metal cation that is able to form a precipitation product with an anion of the near-infrared-absorbing dye, and forms a water-insoluble salt of the near-infrared-absorbing dye; and a second step, in which a dispersion in which the water-insoluble salt of the near-infrared-absorbing dye is dispersed is mixed with an aqueous solution comprising a polymeric surfactant and then supports the water-insoluble salt of the near-infrared-absorbing dye in a particle of the polymeric surfactant.

A second aspect of the present invention provides a near-infrared-absorbing composite particle comprising:

a water-insoluble salt of a near-infrared-absorbing dye, which comprises:

an anion of the near-infrared-absorbing dye; and a metal cation capable of forming a precipitation product with the anion of the near-infrared-absorbing dye; and a particle of a polymeric surfactant, in which a water-insoluble salt of the near-infrared-absorbing dye is supported in the hydrophobic part of the polymeric surfactant, wherein the near-infrared-absorbing composite particle exhibits a photothermal effect photoacoustic signal or both upon photoirradiation.

A third aspect of the present invention provides a method for using the near-infrared-absorbing composite particle of the second aspect as a photothermal therapeutic agent, a diagnostic agent, an imaging or mapping probe, a drug carrier, or a combination thereof that absorbs light in the near-infrared region and generates heat.

A fourth aspect of the present invention provides a method for photothermal treatment, comprising:

(a) administering the near-infrared-absorbing composite particle of the second aspect to a patient; and (b) applying photoirradiation to allow the near-infrared-absorbing composite particle to absorb light in the near-infrared region and generate heat.

A fifth aspect of the present invention provides a method for realizing photothermal or photoacoustic imaging or mapping, comprising:

(a) administering the near-infrared-absorbing composite particle of the second aspect to a subject; and (b) applying photoirradiation to allow the near-infrared-absorbing composite particle to absorb light in the near-infrared region and generate heat and thereby provide a photothermal or photoacoustic signal or image.

Hereinafter, the present invention will be described in detail.

According to the present invention, the near-infrared-absorbing composite particle which exhibits a photothermal effect and/or photoacoustic signal upon photoirradiation comprises:

a water-insoluble salt of a near-infrared-absorbing dye, which comprises:

anions of the near-infrared-absorbing dye; and metal cations capable of forming a precipitation product with the anions of the near-infrared-absorbing dye; and a particle of a polymeric surfactant, in which a water-insoluble salt of the near-infrared-absorbing dye is supported in the hydrophobic part of the polymeric surfactant.

The near-infrared-absorbing composite particles according to the present invention can exhibit a photothermal effect in which the near-infrared-absorbing composite particle absorbs light in the near-infrared region and generates heat via a water-insoluble salt, and the near-infrared-absorbing composite particles can generate a photoacoustic signal based on the photothermal effect. Accordingly, the nearinfrared-absorbing composite particle according to the present invention may be used as a photothermal therapeutic agent, a diagnostic agent, an imaging or mapping probe, a drug carrier, or a combination thereof that absorbs light in the near-infrared region and generates heat.

The near-infrared-absorbing composite particle according to the present invention can have a role as a heat source which can be heated to a temperature of 45° C. or higher, preferably 50° C. or higher, and more preferably 60° C. or higher, through the photothermal effect. Accordingly, the near-infrared-absorbing composite particles according to the present invention can be used as a probe for mapping and/or imaging capable of providing a temperature profile where near-infrared-absorbing composite particles are located, as well as a heat source for photothermal therapy.

The near-infrared-absorbing composite particles according to the present invention may be nanoparticles, capable of solving the problem of the conventional near-infrared-absorbing dyes described above, which can be dispersed to colloidal particles by maintaining a structural form in bodily fluids (e.g., blood). For example, in the present invention, the nanoparticles may have a diameter of 1 nm to 100 nm, preferably 1 nm to 50 nm, and more preferably 10 nm to 30 nm. The near-infrared-absorbing composite particles according to the present invention may not contain a polyol, a hydrophobic polymer, or a combination thereof.

To solve the problems of the existing near-infrared-absorbing dyes described above, the method for preparing a near-infrared-absorbing dye-based composite particle, comprising:

a first step, in which an ionizable near-infrared-absorbing dye, that is in a state dissolved in an aqueous medium, undergoes a precipitation reaction with an ionic compound capable of providing a metal cation that is able to form a precipitation product with an anion of the near-infrared-absorbing dye, and forms a water-insoluble salt of the near-infrared-absorbing dye; and a second step, in which a dispersion in which the water-insoluble salt of the near-infrared-absorbing dye is dispersed is mixed with an aqueous solution comprising a polymeric surfactant and then supports the water-insoluble salt of the near-infrared-absorbing dye in a particle of the polymeric surfactant (e.g., inside thereof).

In this Example, the near-infrared-absorbing composite particles were prepared according to the preparation method of the present invention, in which ionizable indocyanine green (ICG) was used in a water medium as a near-infrared-absorbing dye and iron ions were used as metal cations. As a result, it was discovered that the thus-prepared near-infrared-absorbing composite particles have improved colloidal stability, photostability, photothermal efficiency, and photoacoustic signal compared to indocyanine green (ICG). The present invention is based on these findings.

The method for preparing near-infrared-absorbing composite particles according to the present invention can provide near-infrared-absorbing dye-based composite particles which exhibit inhibition of non-specific aggregation, inhibition of absorption into serum proteins, inhibition of photodegradation, or a combination thereof, compared to the ionizable near-infrared-absorbing dye of the first step. Additionally, near-infrared-absorbing composite nanoparticles can be provided which can be dispersed into colloidal particles in bodily fluids (e.g., blood).

In the present invention, the first step is a step in which an ionizable near-infrared-absorbing dye, that is in a state dissolved in an aqueous medium, undergoes a precipitation reaction with an ionic compound capable of providing metal cations that can form a precipitation product with anions of a near-infrared-absorbing dye, and forms a water-insoluble salt of the near-infrared-absorbing dye. For example, through the precipitation, the water-insoluble salt of the near-infrared-absorbing dye can be separated in the first step.

Through the first step, the hydrophobic near-infrared-absorbing dye can be modified into a hydrophobic, water-insoluble, or poorly water-soluble near-infrared-absorbing dye. For example, the precipitate as a poorly soluble material may be a material having a solubility of 0.01 mol/L or less, but the precipitate is not limited thereto.

In the first step, the ionizable near-infrared-absorbing dye may be at least one selected from the group consisting of hydrophilic cyanine dye containing a sulfonate group, indocyanine green (ICG), cyanine 5.5 (Cy5.5), and cyanine 7 (Cy7). Preferably, the near-infrared-absorbing dye may be indocyanine green.

In the first step, the ionizable near-infrared-absorbing dye may be an ionic compound, for example, a soluble salt. The soluble salt may be a compound containing a metal ion (e.g., $Li^+$, $Na^+$, $K^+$, $Rb^+$, or $Cs^+$) and an ammonium ion ($NH_4^+$), but the compound is not limited thereto.

In the first step, the ionic compound which provides metal cations that can form a precipitation product with anions of a near infrared absorbing dye may be a soluble salt. The soluble salt may be a compound containing an ammonium ion ($NH_4^+$), a nitrate ($NO_3^-$), a bicarbonate ($HCO_3^-$), a chlorate ($ClO_3^-$), a halide ($Cl^-$, $Br^-$, $I^-$), or a sulfate ($SO_4^{2-}$), but the soluble salt is not limited thereto.

Examples of the metal cations that can form a precipitation product with anions of a near-infrared-absorbing dye may be an iron ion.

In the present invention, the second step is a step in which a dispersion, in which the water-insoluble salt of the near-infrared-absorbing dye is dispersed, is mixed with an aqueous solution containing a polymeric surfactant, and the water-insoluble salt of the near-infrared-absorbing dye is then supported in the particles of the polymeric surfactant, and preferably on the inside of the particles of the polymeric surfactant.

Generally, surfactants are compounds that have a hydrophilic part which is soluble in water and a hydrophobic part which is soluble in oil. Surfactant molecules, at a certain concentration or higher, aggregate together and form structures called micelles. Meanwhile, the hydrophobic part of each surfactant is miscible with a water-insoluble salt of a near-infrared-absorbing dye and thus can support a water-insoluble salt in a surfactant-based particle or particle containing a surfactant.

The polymeric surfactant may have a molecular weight of 7,500 to 15,000.

Non-limiting examples of the polymeric surfactant to be used in the present invention may be at least one selected from the group consisting of a polyoxyethylene polyoxypropylene copolymer, a polyoxyethylene-sorbitan-fatty acid ester, polyoxyethylene stearic acid ester, sodium dioctylsulfosuccinate, sodium lauryl sulfate, phospholipids, a propylene glycol mono-fatty acid ester, a propylene glycol di-fatty acid ester, a polyalkylene polyol, a mono-glyceride, a di-glyceride, a sorbitan fatty acid ester, and a sterol. Preferably, the surfactant may be a polyoxyethylene polyoxypropylene copolymer.

Additionally, in the polyoxyethylene polyoxypropylene copolymer, the addition ratio between polyethylene oxide (PEO) and polypropylene oxide (PPO) may be in a ratio of 2.5 to 6:1.

In the second step, non-limiting examples of the dispersant that can disperse the water-insoluble salt of the near-infrared-absorbing dye may be an alcohol, a carboxylic acid, tetrahydrofuran, acetonitrile, acetone, dimethylsulfoxide, dimethylformamide, hexamethylphosphoramide, or a mixture thereof.

The second step may not only support the water-insoluble salt of the near-infrared-absorbing dye in the particles of a polymeric surfactant, but may also further support, in the particles of the polymeric surfactant, an additive selected from the group consisting of a therapeutic agent, a diagnostic agent, and a contrast agent. In particular, when the additive is hydrophobic, the additive may be supported in a dispersion, whereas when the additive is hydrophilic, the additive may be dispersed/dissolved in an aqueous solution containing a polymeric surfactant. As such, the additive may be supported in polymeric surfactant particles including a hydrophilic part and a hydrophobic part through the second step.

Accordingly, the near-infrared-absorbing composite particle according to the present invention may be one in which an additive (drug) selected from the group consisting of a therapeutic agent, a diagnostic agent, and a contrast agent is further supported in the particle of the polymeric surfactant. Accordingly, the near-infrared-absorbing composite particle according to the present invention can act as a drug carrier, and additionally, can release a drug due to a photothermal effect upon photoirradiation.

Non-limiting examples of an anticancer agent, in an embodiment of the drug to be supported, may include an alkylating agent which can inhibit DNA synthesis by forming a covalent bond with a nucleic acid. The alkylating agent may be at least one selected from the group consisting of mechlorethamine, cyclophosphamide, ifosfamide, melphalan, chlorambucil, busulfan, thiotepa, nitrosourea, and a platinum compound, and most preferably cisplatin or carboplatin.

In the present invention, based on 100 parts by weight of the near-infrared-absorbing composite particles, the anions of the near-infrared-absorbing dye may be contained in an amount of 0.4 to 40 parts by weight, and preferably 1 to 10 parts by weight; the metal cations of the near-infrared-absorbing dye may be contained in an amount of 0.1 to 10 parts by weight, and preferably 0.1 to 2 parts by weight; and the polymeric surfactant may be contained in an amount of 50 to 99.5 parts by weight, preferably 80 to 99.5 parts by weight, and more preferably 90 to 99.5 parts by weight.

Furthermore, the near-infrared-absorbing composite particle according to the present invention may be formulated by further containing a suitable excipient and a diluent. For example, the near-infrared-absorbing composite particle according to the present invention may be used by formulating in the form of an oral formulation (e.g., powders, granules, tablets, capsules, suspensions, emulsions, syrups, aerosols, etc.), an agent for external use, a suppository, and a sterile injection solution.

The present invention provides a method for photothermal treatment, which comprises:

(a) administering the near-infrared-absorbing composite particle of according to the present invention to a patient (in vivo application); and (b) applying photoirradiation to allow the near-infrared-absorbing composite particle to absorb light in the near-infrared region and generate heat.

By the application of the above method, for example, in the method for photothermal treatment of cancer of the present invention, step (a) may be a step to administer the near-infrared-absorbing composite particles to the blood vessel of a patient to be accumulated in cancer cells, and step (b) may be a step to perform a photothermal treatment of cancer cells via photoirradiation.

The method for photothermal treatment is non-destructive, simple, and has fewer side effects compared to a surgical operation. Additionally, the method for photothermal treatment has advantages in that the method does not require general anesthesia, causes almost no pain for the patient, and the period for stabilization and recovery is short, and further, several repeated treatments are possible.

When the near-infrared-absorbing composite particles according to the present invention are used, it is possible to perform photothermal therapy (PTT), such as apoptosis, by heat generated through photoirradiation. Such photothermal therapy is a widely used clinical method for cancer treatment because it has few side effects, is non-invasive, and is specific to light of a particular wavelength. In particular, the heat generated may be at a temperature of about 45° C. or higher, preferably 50° C. or higher, and more preferably 60° C. or higher, at which apoptosis may occur at a rate of 90% or higher or 95% or higher. In particular, as the amount of accumulation of the near-infrared-absorbing composite particles based on the indocyanine green increases at the treatment site, such as the lymph node where the tumor has developed, the amount of heat generation also increases, and thus heat which is greater than the amount sufficient for major cell destruction is generated, thereby causing apoptosis.

Additionally, the present invention provides a method for realizing photothermal or photoacoustic imaging or mapping, which comprises:

(a) administering the near-infrared-absorbing composite particle according to the present invention to a subject (e.g., a suspected patient) (in vivo administration); and (b) applying photoirradiation to allow the near-infrared-absorbing composite particle to absorb light in the near-infrared region and generate heat and thereby provide a photothermal or photoacoustic signal or image.

The examination of living tissues and organs is very important for diagnosing disease and monitoring the results of treatment. However, optical visualization of tissues and organs deep within the body is difficult due to light scattering in living tissues.

Meanwhile, 1-, 2-, or 3-dimensional images of living tissues may be formed by applying the image restoration algorithm. The photoacoustic tomography (PAT) device is a non-invasive imaging device that utilizes a photoacoustic effect, and it can realize functional images, metabolic images, and molecular and genetic images as well as structural images of in vivo tissues (in the human body) using optical characteristics and ultrasonic characteristics.

Examples of the photoacoustic imaging system may include (1) single-cell images in vivo (e.g., red blood cells and melanoma cells), (2) vascular and lymph node network images, (3) monitoring of angiogenic blood vessels, (4) mapping of oxygen saturation level of microvascular hemoglobin, (6) images of metabolic rates, (7) images of functional brain activities, (8) monitoring of drug delivery and treatment responses, (9) molecular imaging using biomarkers and contrast agents, (10) images of gene expression, etc. Furthermore, current clinical trials are mainly performed on the images of lymph nodes for the imaging of breast cancer and melanoma and for the determination of metastasis of breast cancer. Additionally, examples of possible potential clinical applications of the photoacoustic imaging system may include (1) images of prostate gland, thyroid gland, head and neck cancer, (2) diagnosis of peripheral and cardiovascular disease, (3) monitoring of early responses after treatment of cancer, (4) images of functional human neurons, (5) images of the gastrointestinal tract using an endoscope, (6) cardiovascular images using a catheter, (7) monitoring of arthritis and inflammation, (8) images of unstained tissue sections, (9) images of migrating cells in vivo, etc.

In the present invention, step (b) may be a step to perform percutaneous irradiation of light with a wavelength of 600 nm to 1,000 nm.

In the present invention, the light wavelength at the time of photoirradiation may be in a range of 600 nm to 1,000 nm. When the wavelength is shorter than 600 nm, the laser wavelength is too short to penetrate deeply into living tissues, and thus, photothermal treatment is possible only in the area near the skin. In contrast, when the wavelength is longer than 1,000 nm, photothermal treatment is not desirable because interference increases due to absorption of water excessively present in the living body. Additionally, photoirradiation may be performed by a lamp or laser.

Advantageous Effects

The near-infrared-absorbing dye-based composite particles provided in the present invention which exhibit a photothermal effect have advantages in that they have improved colloidal stability and photostability, have improved photothermal and photoacoustic efficiencies, exhibit a characteristic of cancer cell-specific accumulation without exhibiting biotoxicity, and thus can be effectively used as a cancer therapeutic agent or drug carrier.

DETAILED DESCRIPTION OF THE INVENTION

Example 1: Preparation of ICG-Encapsulated Nanoparticles

The ICG-encapsulated nanoparticles according to the present invention were prepared, for example, such that the ICG, which shows absorption/fluorescence in the near-infrared region and simultaneously has a photothermal effect, can be present inside of the polymer nanoparticles in a stable state and have improved optical characteristics. The compositions of these particles and the specific preparation methods are as follows.

Example 1-1. Preparation of Hydrophobic ICG-Fe Composite which can be Loaded into Hydrophobic Inside of Polymer Nanoparticles 20 mg of indocyanine green (ICG, MW: 774.96, Tokyo Chemical Industry, Japan) and 30 mg of iron(III) chloride ($FeCl_3$, MW: 162.2, Sigma-Aldrich, USA) were each dissolved in 20 mL of water, and then the two solutions were mixed together. The mixture was reacted at room temperature for 1 hour, and the supernatant was removed when the precipitation product had sedimented. The precipitated ICG-Fe composite was washed with an excess amount of water. The purified ICG-Fe composite was dried at room temperature under vacuum. The thus-prepared ICG-Fe composite was used to prepare nanoparticles in Example 1-2.

Figure 2:
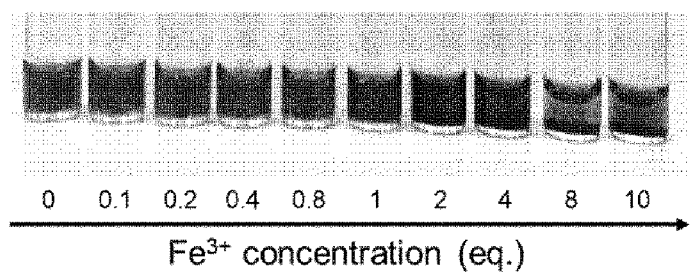
FIG. 2 shows (a) an image illustrating the formation of a hydrophobic ICG-Fe composite according to an embodiment of the present invention; and (b) the results of the formation confirmed by the absorption/fluorescence spectrum.
Figure 2:
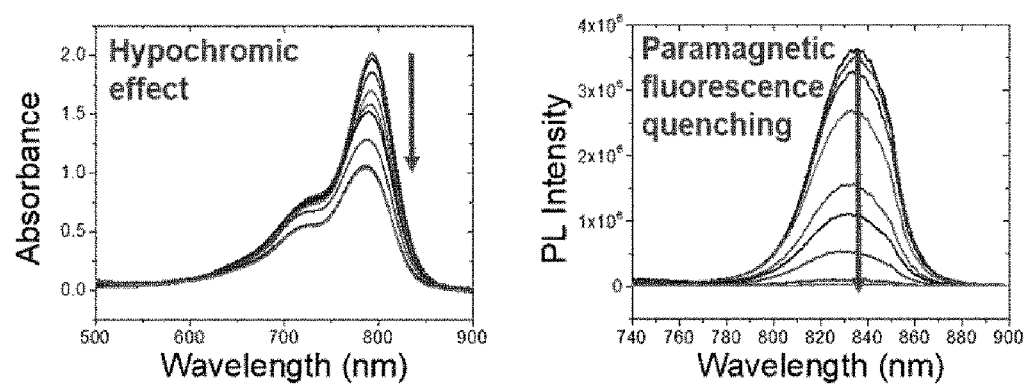

Additionally, to confirm the binding of ICG with iron ions, the changes in the addition of iron ions at various concentrations to a certain amount of ICG were shown by way of images and absorption/fluorescence spectra. As shown in FIG. 2, it was confirmed that as the amount of iron ions increased, the hydrophobicity of ICG, which was well dispersed in water, increased to form a precipitate. Additionally, the absorption/fluorescence spectra showed that absorption decreased with the increase of the amount of iron ions and fluorescence was not shown, thus confirming that a hydrophobic composite was formed by the binding of ICG with iron ions. Additionally, it was confirmed that ICG and iron ions were present in the ICG-Fe composite at a binding ratio (molar ratio) of 3:1 using ICP-OES mass spectrometry and absorption spectra.

Example 1-2. Preparation of Nanoparticles Containing ICG-Fe Composite 0.5 mg of the ICG-Fe composite prepared according to Example 1-1 was dissolved in 20 μL of dimethyl sulfoxide (DMSO, Daejung Chemical & Metals Co., Ltd., Korea), and the resultant was added to 1 mL of an aqueous solution, in which Pluronic F127 (10 mg, Sigma-Aldrich, USA) as a polymeric surfactant was mixed, while dispersing by ultrasonic waves, and thereby ICG-Fe complex-encapsulated nanoparticles (ICG-Fe NPs) were prepared.

Figure 1:
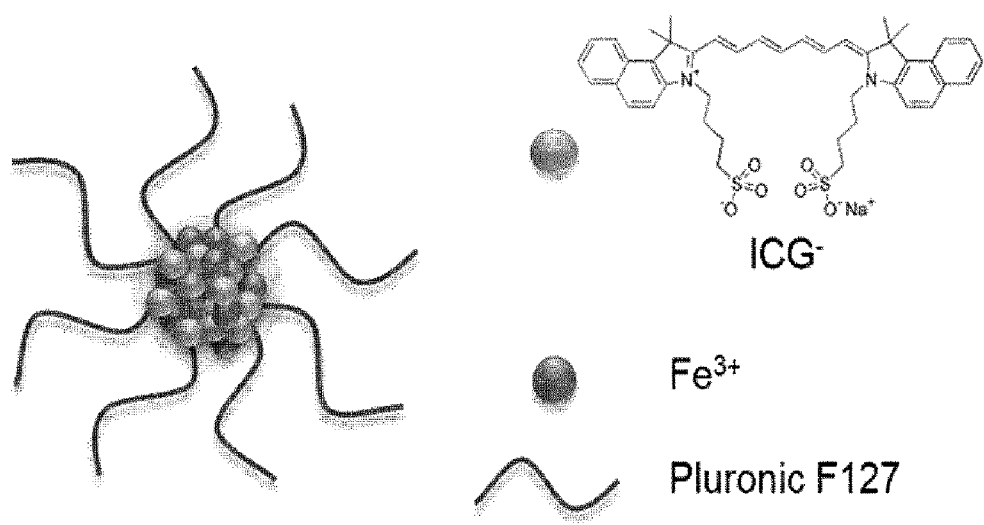
FIG. 1 shows a chemical structure of a near-infrared fluorescent dye, indocyanine green (ICG), according to an embodiment of the present invention; and a schematic diagram illustrating the design of finally prepared nanoparticles in which ICG is encapsulated.
Figure 3:
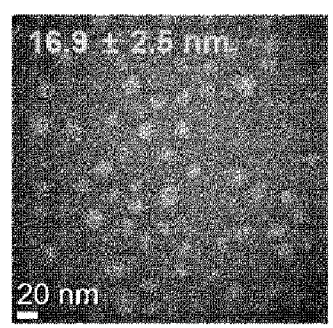
FIG. 3 shows (a) a transmission electron microscope (TEM) image and (b) the results of the absorption/fluorescence spectrum of ICG-Fe-encapsulated nanoparticles (ICG-Fe NPs) including a hydrophobicized ICG-Fe composite according to an embodiment of the present invention.
Figure 3:
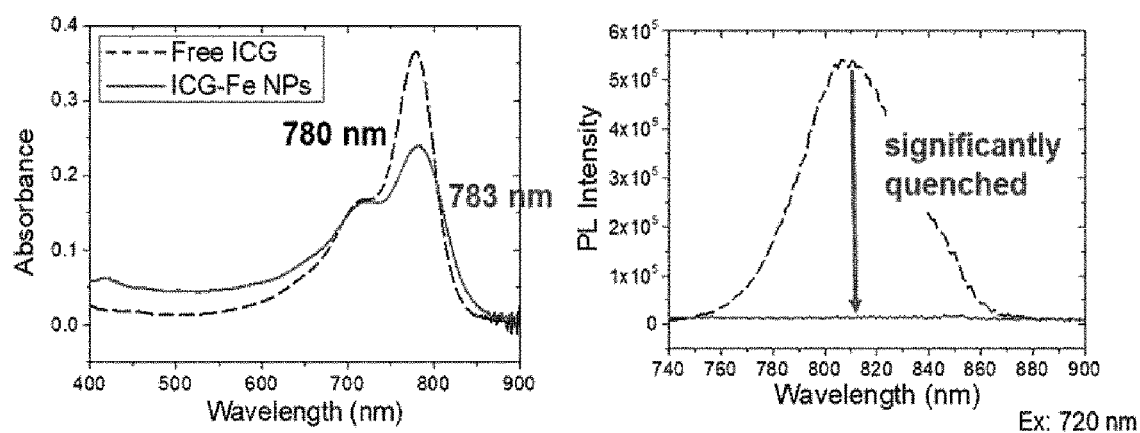

The schematic diagram of the design of the thus-prepared ICG-Fe NPs is shown in FIG. 1. The structure and morphology of the prepared nanoparticles were analyzed using transmission electron microscopy and absorption/fluorescence spectrum analysis, and the results are shown in FIG. 3. As shown in FIG. 3, the average diameter of the ICG-Fe NPs calculated from the TEM image was about 17 nm. The absorption/fluorescence spectrum of ICG was observed to confirm whether the ICG-Fe composite was encapsulated inside the prepared nanoparticles. The ICG absorption spectrum of the nanoparticles shifted to long wavelengths and fluorescence was hardly observed compared to the aqueous solution of ICG. From this result, it was confirmed that ICG was present inside of the nanoparticles.

Figure 4:
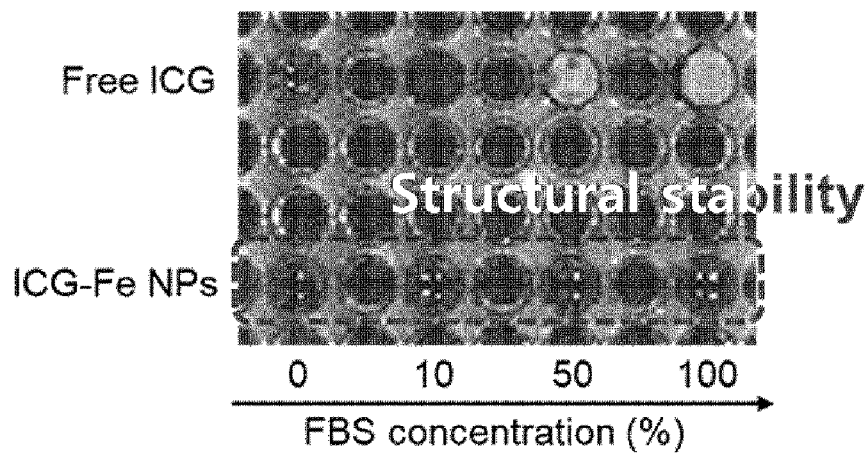
FIG. 4 shows (a) a fluorescence image illustrating the ICG-Fe NPs according to an embodiment of the present invention with regard to their colloidal stability in a biomimetic environment via a fluorescence imaging device (IVIS); and (b) a graph illustrating the intensity of the fluorescence signals detected therefrom.
Figure 4:
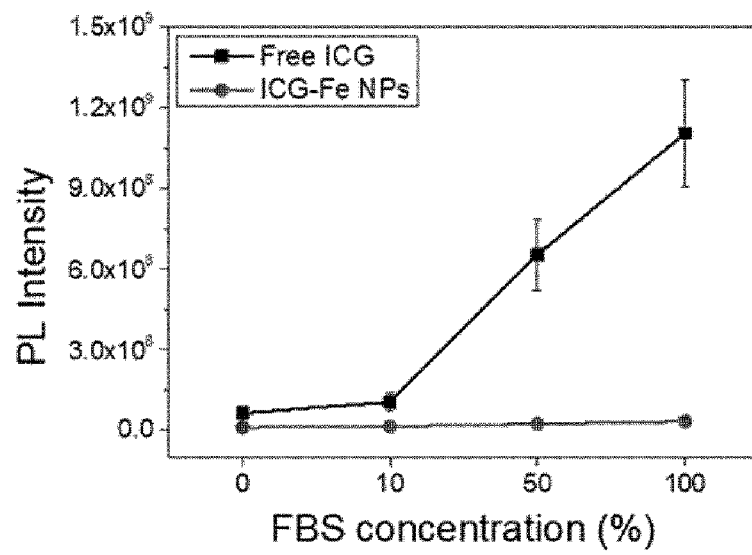

Example 2: Evaluation of ICG-Fe NPs with Regard to Colloidal Stability and Photostability Example 2-1. Evaluation of ICG-Fe NPs with Regard to Colloidal Stability in the Presence of Albumin To confirm whether the ICG-Fe NPs prepared according to Example 1-2 can maintain colloidal stability even in the presence of albumin, which is a biomimetic environment, using the aqueous solution of ICG as the control group, the ICG-Fe NPs were each mixed with serum albumin (fatal bovine serum; FBS) at different concentrations, and the changes were observed on a 96-well plate using a fluorescence imaging device (IVIS). The results are shown in FIG. 4. As shown in FIG. 4, it was confirmed that the prepared ICG-Fe NPs were stably present while maintaining their structural form through the sustained fluorescence-quenching property, although the amount of serum albumin increased. In contrast, it was confirmed that ICG forms a dimer in an aquatic environment and partially exhibits a fluorescence-quenching property, and thus, ICG returned to a monomolecular state as it was exposed to high affinity proteins, thereby recovering fluorescence. These results indicate that the ICG bound to the iron ions is effectively encapsulated into the hydrophobic interior of the nanoparticles, and thereby the effect on the external ICG is reduced.

Figure 5:
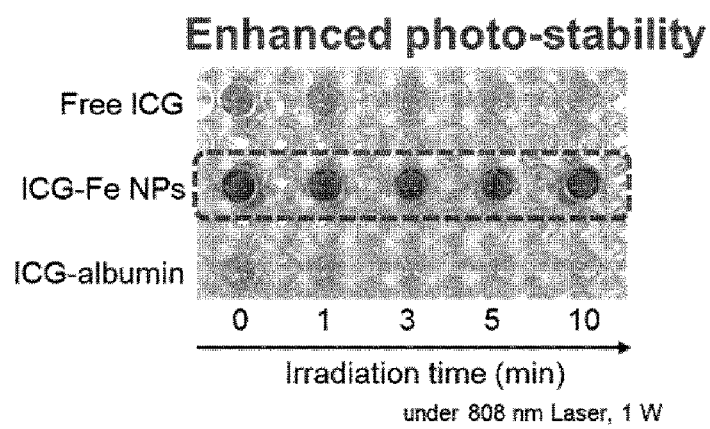
FIG. 5 shows the evaluation results of the ICG-Fe NPs according to an embodiment of the present invention with regard to their photostability in the presence of light, in which (a) shows an image illustrating changes in color; and (b) shows graphs illustrating the degree of changes in relative absorption/fluorescence signals, after photoirradiation, respectively.
Figure 5:
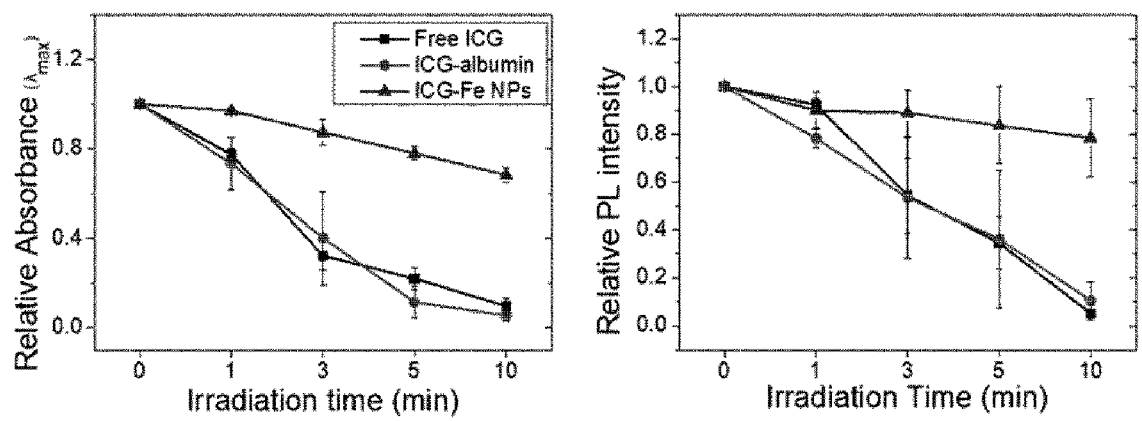

Example 2-2. Evaluation of Photostability of ICG-Fe NPs at the Time of Photoirradiation To confirm whether the ICG-Fe NPs prepared according to Example 1-2 can maintain photostability at the time of photoirradiation, the changes in color and absorption/fluorescence signal intensity after irradiation with a laser (808 nm, 1 W) were examined, and the results are shown in FIG. 5. As shown in FIG. 5, it was confirmed that the prepared ICG-Fe NPs maintained their unique color even after laser irradiation for a certain period of time, compared to the aqueous solution of ICG and the ICG-albumin conjugate. Furthermore, based on the above result that the absorption/fluorescence signal intensity of the prepared ICG-Fe NPs was maintained even after laser irradiation at a level similar to that before laser irradiation, it was confirmed that the prepared ICG-Fe NPs have a greater improvement than the two control groups. These results are due to the fact that the nanoparticles were formed immediately as the iron ions were bound to ICG, and thereby the photodegradation by light was reduced.

Figure 6:
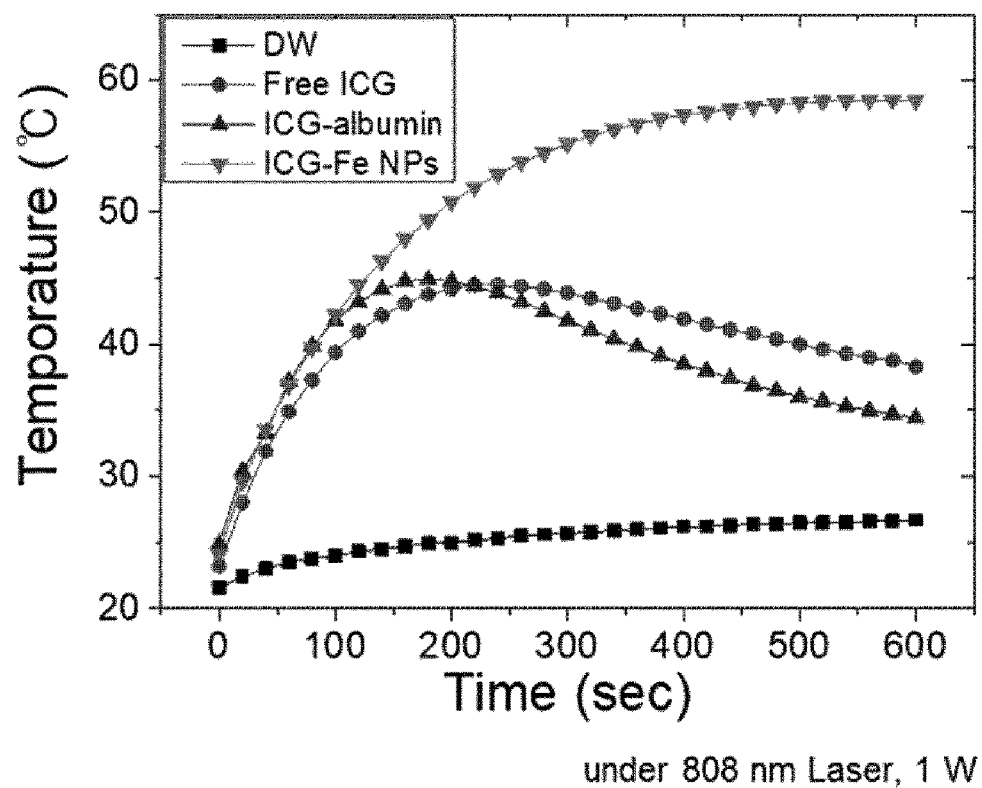
FIG. 6 shows a graph illustrating the photothermal properties by comparing the degree of a temperature increase of the ICG-Fe NPs according to an embodiment of the present invention.

Example 3: Evaluation of Photothermal and Photoacoustic Characteristics of ICG-Fe NPs To confirm the photothermal efficiency of the ICG-Fe NPs prepared according to Example 1-2, the ICG-Fe NPs were irradiated with a laser (808 nm, 1 W) and the temperature of the solution was measured after irradiation. The results are shown in FIG. 6. As shown in FIG. 6, when the photothermal efficiencies were compared by having the aqueous solution of ICG and the ICG-albumin conjugate, which have similar absorbance, as control groups, it was confirmed that the prepared ICG-Fe NPs showed a temperature increase similar to those of the control groups at the beginning of laser irradiation, but the temperature of the prepared ICG-Fe NPs was maintained at about 60° C. under laser irradiation continued for 10 minutes. In contrast, it was confirmed that the two control groups showed a temperature increase to about 45° C. at the beginning of laser irradiation and then showed a phenomenon of temperature decrease due to photodegradation. Such an increase of photothermal efficiency of the ICG-Fe NPs is thought to be due to fluorescence of ICG, which competitively acts on the photothermal reaction and is present within the nanoparticles in a fluorescence-quenched state.

Figure 7:
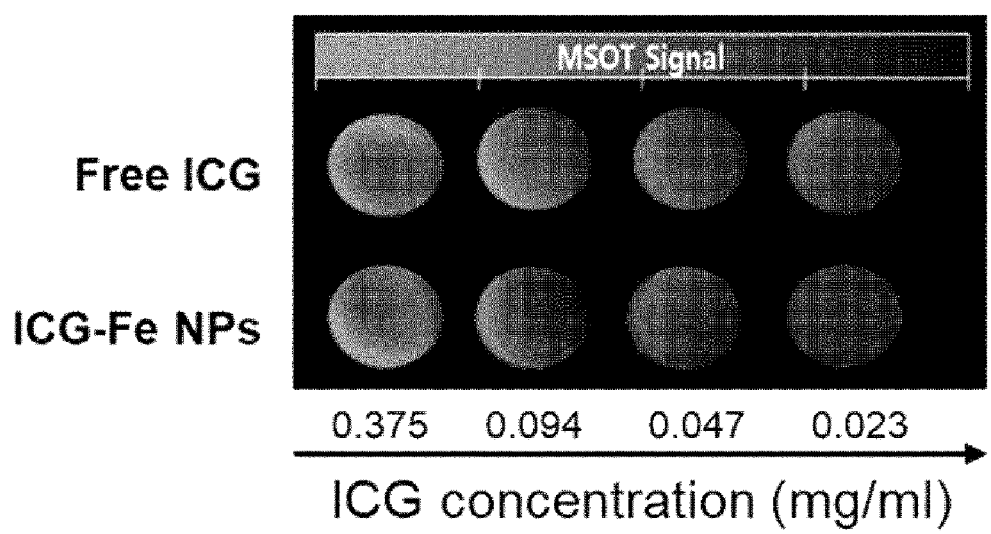
FIG. 7 shows an image illustrating the photoacoustic image signals of the ICG-Fe NPs according to an embodiment of the present invention.

The increase in the photothermal efficiency may cause an improvement of the photoacoustic characteristic that occurs based on the photothermal effect. To confirm the photoacoustic characteristic of the prepared ICG-Fe NPs, the photoacoustic signal image of the nanoparticles obtained by the multispectral optoacoustic tomography (MSOT) device is shown in FIG. 7. As shown in FIG. 7, it was confirmed that ICG-Fe NPs show a photoacoustic signal.

Example 4: Evaluation of Toxicity of ICG-Fe NPs in Animal Models

Figure 8:
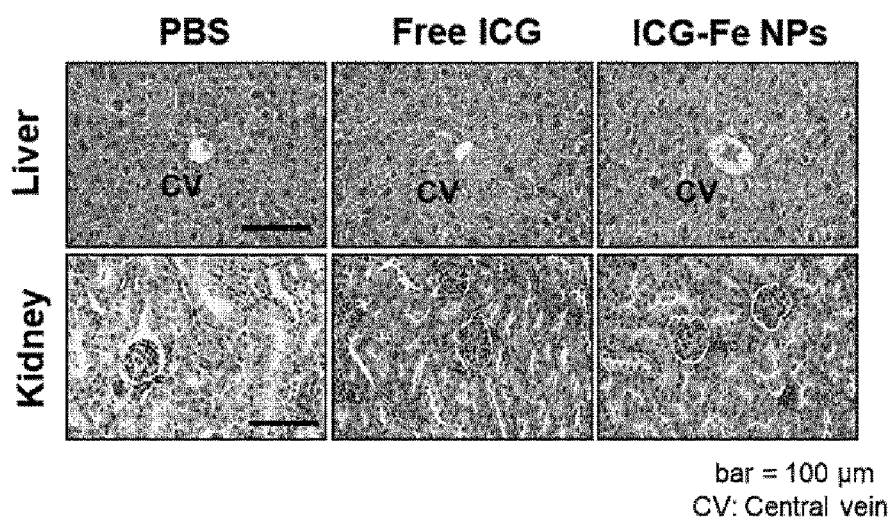
FIG. 8 shows the results of confirming the presence/absence of in vivo toxicity of the ICG-Fe NPs according to an embodiment of the present invention by (a) blood liver levels and (b) a liver/kidney tissue staining method.

200 μL of PBS and an aqueous solution of ICG, as control groups, and the ICG-Fe NPs prepared according to Example 1-2 were each intravenously injected to 5-week-old male nude mice (Orientbio Inc., Korea). Two days later, blood and liver/kidney tissues were collected and evaluated for toxicity. The blood liver levels and the tissue images observed by immunostaining are shown in FIG. 8. As shown in FIG. 8, the AST/ALT values for 3 groups of materials were shown to be at normal levels, and no abnormalities were found in immunostained liver/kidney tissues. These results indicate that the ICG-Fe NPs according to the present invention do not exhibit toxicity in a living environment.

Figure 9:
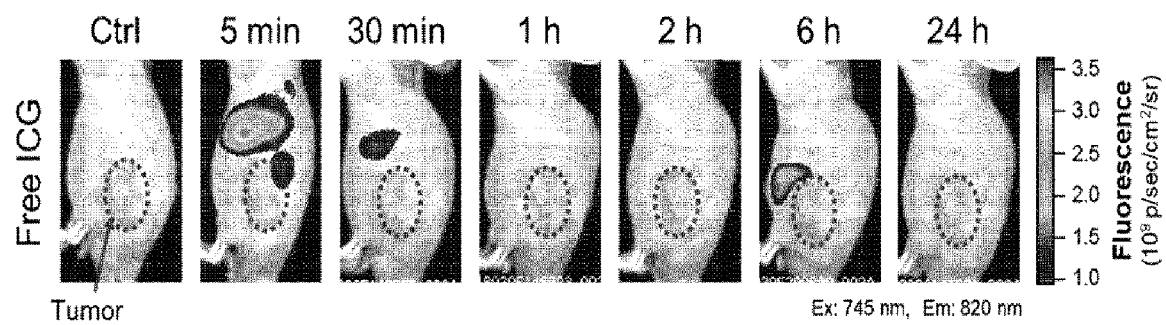
FIG. 9 shows images illustrating the presence/absence of a characteristic of accumulation in cancer cells via fluorescence imaging in a cancer model mouse administered with the ICG-Fe NPs according to an embodiment of the present invention. The red arrows indicate the location of the cancer tissues.
Figure 9:
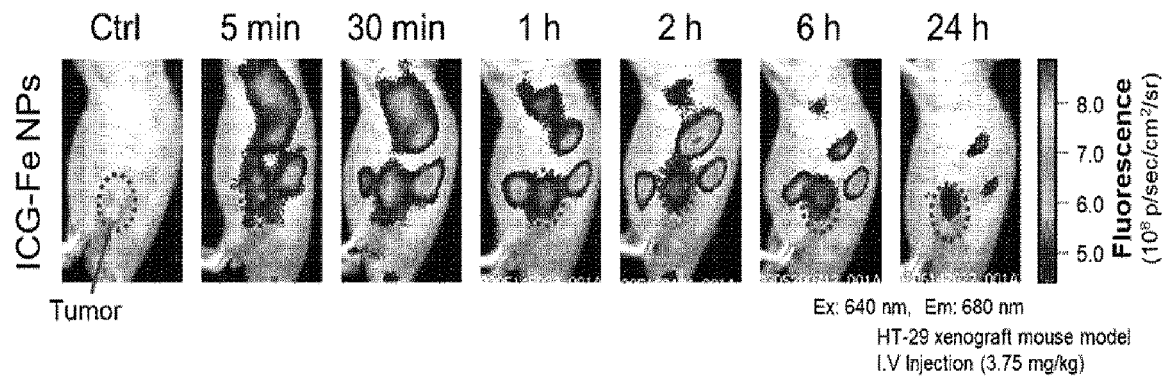

Example 5: Evaluation of Characteristic of ICG-Fe NPs of Cancer Cell Accumulation in Cancer Disease Model and Photothermal Therapy Example 5-1. Evaluation of Characteristic of ICG-Fe NPs of Cancer Cell Accumulation in Cancer Disease Model Via Fluorescence Imaging The model with a cancer disease was prepared by subcutaneous injection of $1\times10^7$ HT-29 cells (human colon cancer, Korean Cell Line Bank) on the left thigh of 5-week-old male nude mice (Orientbio Inc., Korea). After 2 weeks of cancer cell transplantation, solid tumors were confirmed to be formed, and then subsequent experiments were performed. Since the ICG-Fe NPs prepared according to Example 1-2 did not exhibit a fluorescence characteristic, 200 µL of nanoparticles, which were prepared by introducing Cy5.5 (a different fluorescent material), were intravenously injected. Fluorescence imaging was performed before/after administration of the nanoparticles, and the results are shown in FIG. 9. As shown in FIG. 9, while the mouse injected with the ICG solution (control group) did not show fluorescence at the cancer site, the mouse injected with Cy5.5-labeled nanoparticles showed fluorescence due to the accumulation of the nanoparticles at the cancer site. These results indicate that ICG-Fe NPs according to the present invention have a characteristic of selective accumulation in cancer tissues.

Figure 10:
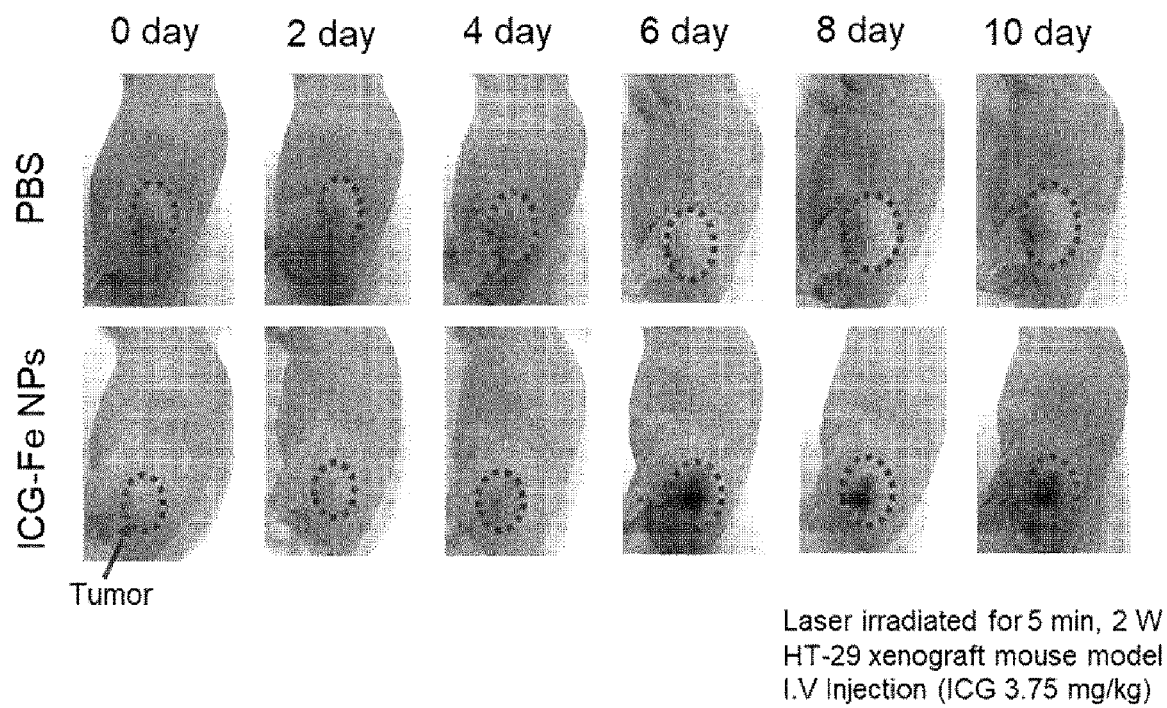
FIG. 10 shows images illustrating the effect of photothermal therapy in a cancer model mouse administered with the ICG-Fe NPs according to an embodiment of the present invention. The red arrows indicate the location of the cancer tissues.

Example 5-2. Evaluation of Photothermal Therapy Effect of ICG-Fe NPs in Cancer Disease Model To mice model of cancer disease prepared according to Example 5-1, 200 µL of ICG-Fe NPs prepared according to Example 2 and PBS were intravenously injected, and 1 and 6 hours thereafter, a partial laser treatment (808 nm, 2 W, 5 min) was performed on the cancer site. Material injections and laser treatments were repeated 3 times at 2 day intervals, and the results are shown in FIG. 10. As shown in FIG. 10, when 3 treatments were performed after the injection, the cancer model injected with PBS showed no therapeutic effect, whereas the mice injected with the nanoparticles showed a thrombosis in the cancer site due to the effect of hyperthermia treatment. These results indicate that the ICG-Fe NPs according to the present invention can be used for phototherapy of cancer.

The invention claimed is:

1. A method for preparing a near-infrared-absorbing dye-based composite particle, comprising:
reacting an ionizable near-infrared-absorbing dye dissolved in an aqueous medium with an ionic compound comprising a metal cation dissolved in an aqueous medium to form a precipitation product,
wherein the metal cation of the ionic compound reacts with an anion of the near-infrared-absorbing dye to form the precipitation product, and wherein the precipitation product comprises a water-insoluble salt of the near-infrared-absorbing dye;
washing the precipitation product;
dispersing the washed precipitation product in a solvent to prepare a dispersion comprising the water-insoluble salt of the near-infrared-absorbing dye; and
mixing the dispersion comprising the water-insoluble salt of the near-infrared-absorbing dye with an aqueous solution comprising a polymeric surfactant to form the near-infrared-absorbing dye-based composite particle,
wherein the near-infrared-absorbing dye-based composite particle comprises the water-insoluble salt of the near-infrared-absorbing dye encapsulated in a particle of the polymeric surfactant.

2. The method of claim 1, wherein the near-infrared-absorbing dye-based composite particle further comprises, encapsulated in the particle of the polymeric surfactant, an additive selected from the group consisting of a therapeutic agent, a diagnostic agent, and a contrast agent.

3. The method of claim 1, wherein the metal cation of the ionic compound is an iron ion that forms a precipitation product with the anion of the near-infrared-absorbing dye.

4. The method of claim 1, wherein, in the first step, the ionizable near-infrared-absorbing dye is at least one selected from the group consisting of a hydrophilic cyanine dye comprising a sulfonate group, indocyanine green (ICG), cyanine 5.5 (Cy5.5), and cyanine 7 (Cy7).

5. The method of claim 1, wherein the near-infrared-absorbing dye-based composite particle is a near-infrared-absorbing dye-based composite particle that exhibits a photothermal effect or photoacoustic signal upon photoirradiation.

6. The method of claim 1, wherein the near-infrared-absorbing dye-based composite particle being prepared exhibits inhibition of non-specific aggregation, inhibition of absorption into serum proteins, inhibition of photodegradation, or a combination thereof, compared to the ionizable near-infrared-absorbing dye of the first step.

7. A near-infrared-absorbing composite particle comprising:
a water-insoluble salt of a near-infrared-absorbing dye, which comprises
a precipitation product of an anion of the near-infrared-absorbing dye and
a metal cation of an ionic compound; and
a particle of a polymeric surfactant,
wherein the water-insoluble salt of the near-infrared-absorbing dye is encapsulated in the particle of the polymeric surfactant, and
wherein the near-infrared-absorbing composite particle exhibits a photothermal effect, a photoacoustic signal, or both the photothermal effect and the photoacoustic signal, upon photoirradiation.

8. The near-infrared-absorbing composite particle of claim 7, wherein the near-infrared-absorbing dye is indocyanine green (ICG) and the metal cation is an iron ion.

9. The near-infrared-absorbing composite particle of claim 7, wherein the near-infrared-absorbing composite particle is a nanoparticle that is able to be dispersed as a colloidal particle in a bodily fluid.

10. The near-infrared-absorbing composite particle of claim 7, wherein the polymeric surfactant has a molecular weight of 7,500 to 15,000.

11. The near-infrared-absorbing composite particle of claim 7, wherein the particle of the polymeric surfactant further encapsulates an additive selected from the group consisting of a therapeutic agent, a diagnostic agent, and a contrast agent is further supported in.

12. The near-infrared-absorbing composite particle of claim 7, wherein the anion of the near-infrared-absorbing dye is contained in an amount of 0.4 to 40 parts by weight, the metal cation in an amount of 0.1 to 10 parts by weight, and the polymeric surfactant in an amount of 50 to 99.5 parts by weight, relative to 100 parts by weight of the near-infrared-absorbing composite particle.

13. The near-infrared-absorbing composite particle of claim 7, wherein the near-infrared-absorbing composite particle is a heat source that is able to be heated to a temperature of 45° C. or higher through the photothermal effect.

14. The near-infrared-absorbing composite particle of claim 7, wherein the near-infrared-absorbing composite particle is prepared by the method of claim 1.

15. A method for using the near-infrared-absorbing composite particle of claim 7 as a photothermal therapeutic agent, a diagnostic agent, an imaging or mapping probe, a drug carrier, or a combination thereof that absorbs light in the near-infrared region and generates heat.

16. A method for photothermal treatment, comprising:
(a) administering the near-infrared-absorbing composite particle of claim 7 to a patient; and
(b) applying photoirradiation to allow the near-infrared-absorbing composite particle to absorb light in the near-infrared region and generate heat.

17. The method of claim 16, wherein step (a) is a step to administer the near-infrared-absorbing composite particle to the blood vessel of a patient to be accumulated in a cancer cell, and step (b) is a step to perform a photothermal treatment of the cancer cell via photoirradiation.

18. A method for realizing photothermal or photoacoustic imaging or mapping, comprising:
 (a) administering the near-infrared-absorbing composite particle of claim 7 to a subject; and
 (b) applying photoirradiation to allow the near-infrared-absorbing composite particle to absorb light in the near-infrared region and generate heat and thereby provide a photothermal or photoacoustic signal or image.

19. The method of claim 1, wherein the ionic compound comprises the metal cation and an anion,
 wherein the anion comprises an ammonium ion, a nitrate ion, a bicarbonate ion, a chlorate ion, a halide ion, a sulfate ion, or a combination thereof, and
 wherein the metal cation is an iron ion.

\* \* \* \* \*